US012746233B2

(12) United States Patent
Danek

(10) Patent No.: US 12,746,233 B2
(45) Date of Patent: Sep. 29, 2026

(54) REBAMIPIDE FOR USE IN PREVENTION AND/OR TREATMENT OF ARTERIAL STIFFNESS

(71) Applicant: SQUARE POWER LTD., London (GB)

(72) Inventor: Ivan Danek, Cernosice (CZ)

(73) Assignee: SQUARE POWER LTD., London (GB)

( * ) Notice: Subject to any disclaimer, the term of this patent is extended or adjusted under 35 U.S.C. 154(b) by 857 days.

(21) Appl. No.: 17/638,873

(22) PCT Filed: Sep. 10, 2020

(86) PCT No.: PCT/EP2020/075399
§ 371 (c)(1),
(2) Date: Feb. 28, 2022

(87) PCT Pub. No.: WO2021/048314
PCT Pub. Date: Mar. 18, 2021

(65) Prior Publication Data

US 2022/0304999 A1 Sep. 29, 2022

(30) Foreign Application Priority Data

Sep. 11, 2019 (EP) .................................... 19020528

(51) Int. Cl.
*A61K 31/4704* (2006.01)
*A61P 9/00* (2006.01)

(52) U.S. Cl.
CPC ............ *A61K 31/4704* (2013.01); *A61P 9/00* (2018.01)

(58) Field of Classification Search
CPC .............................. A61K 31/4704; A61P 9/00
USPC ......................................................... 514/312
See application file for complete search history.

(56) References Cited

FOREIGN PATENT DOCUMENTS

| | | | | | |
|---|---|---|---|---|---|
| CN | 104768551 | A | | 7/2015 | |
| JP | 2011184429 | A | | 9/2011 | |
| JP | 2015525779 | A | | 9/2015 | |
| WO | WO-2008015959 | A1 | * | 2/2008 | ............. A61K 31/47 |
| WO | 2014021637 | A1 | | 2/2014 | |

OTHER PUBLICATIONS

WO-2008015959 google translation (Year: 2008).*
Hayden et al Journal of vascular diseases, 2025, 4(21) 1-44 (Year: 2025).*
International Search Report for PCT/EP2020/075399 Mailed on Dec. 8, 2020.
Chinese Search Report for CN202080061701.X Mailed on May 11, 2023.
Japanese Office Action for JP2022-513873 Mailed on Jun. 12, 2024.
European Search Report for EP19020528.6 Mailed on Feb. 19, 2020.
European Office Action for EP19020528.6 Mailed on Mar. 20, 2023.
Nakagawa Yuko et al: "Rebamipide improves renal injury by suppression of oxygen radicals in patients of chronic glomerular disease", Journal of the American Society of Nephrology; Annual Meeting of the American Society of Nephrology; San Diego, California, USA; Nov. 5-8, 1995, Williams and Wilkins, Baltimore, MD, USA, vol. 6, No. 3, 1995, p. 397, XP009518965, ISSN: 1046-6673.
Jae Moon Choi A et al: "Rebamipide prevents periarterial blood-induced vasospasm in the rat femoral artery model", Pharmacological Research, vol. 46, No. 5, May 2001, pp. 489-495, XP055669968, GB, ISSN: 1046-6618, DOI: 10.1006/phrs.2001.0815.
Jooeyon Jhun et al: "Rebamipide ameliorates atherosclerosis by controlling lipid metabolism and inflammation", Plos One, vol. 12, No. 2, Feb. 27, 2017, p. e0171674, XP055669489, DOI: 10.1371/journal.pone.0171674.
Jung-Yoon Choe et al: "Rebamipide inhibits tumor necrosis factor-alpha-induced interleukin-8 expression by suppressing the NF-kB signal pathway in human umbilical vein endothelial cells", Inflammation Research; Official Journal Of: the International Association of Inflammation Societies the European Histamine Research Society, Birkhauser-Verlag, BA, vol. 59, No. 12, Jul. 8, 2010, pp. 1019-1026, XP019861315, ISSN: 1420-908X, DOI: 10.1007/S00011-010-0221-5.
Yu Lai et al: "Rebamipide Promotes the Regeneration of Aspirin-Induced Small-Intestine Mucosal Injury through Accumulation of [beta]-Catenin", Plos One, vol. 10, No. 7, Jul. 2, 2015, p. e0132031, XP055669496, DOI: 10.1371/journal.pone.0132031.
Katsunori Iijima et al. "Rebamipide, a cytoprotective drug, increases gastric mucus secretion in human: evaluations with endoscopic gastrin test", Dig Dis Sci. Jul. 2009; 54(7): 1500-7. PMID: 18975081, PMCID: PMC2690849, DOI: 10.1007/s10620-008-0507-4.
Hiroki Urashima et al: "Rebamipide increases the amount of mucin-like substances on the conjunctiva and cornea in the N-acetylcysteine-treated in vivo model" Cornea. Aug. 2004; 23(6):613-9, PMID: 15257002, DOI: 10.1097/01.ico.0000126436.25751.fb.
Yuriko Yasuda-Onozawa et al "Rebamipide upregulates mucin secretion of intestinal goblet cells via Akt phosphorylation", Mol Med Rep. Dec. 2017, 16(6): 8216-8222. PMID: 28983630 DOI: 10.3892/mmr.2017.7647.

(Continued)

*Primary Examiner* — Yevgeny Valenrod
(74) *Attorney, Agent, or Firm* — Rivka Friedman

(57) ABSTRACT

The present invention relates to the use of rebamipide in a method of prevention and/or treatment of arterial stiffness and associated diseases, such as hypertension, heart failure, myocardial infarction, stroke, peripheral arterial disease, renal failure, and chronic kidney disease. Rebamipide may also be used in a method of increasing arterial elasticity.

18 Claims, No Drawings

(56) References Cited

OTHER PUBLICATIONS

Mozos Ioana et al: "Inflammatory Markers for Arterial Stiffness in Cardiovascular Diseases", Frontiers in Immunology, vol. 8, Aug. 31, 2017, p. 1058, XP093031458.

* cited by examiner

REBAMIPIDE FOR USE IN PREVENTION AND/OR TREATMENT OF ARTERIAL STIFFNESS

FIELD OF THE INVENTION

The present invention relates to rebamipide for use in a method of prevention and/or treatment of arterial stiffness, especially in a person suffering from or being at risk of hypertension, heart failure, myocardial infarction, stroke, peripheral arterial disease, renal failure, or chronic kidney disease.

BACKGROUND ART

The walls of large arteries, especially the aorta, lose elasticity over time, and this process results in increased arterial stiffness. This reflects, at least in part, gradual fragmentation and loss of elastin fibers in the arterial wall and accumulation of stiffer collagen fibers, partially as a compensatory mechanism against the loss of arterial elastin and partially due to fibrosis, often accompanied by calcium deposition into both elastin and collagen fibers. The loss of arterial elastic properties is associated with increased risk of cardiovascular events, such as myocardial infarction and stroke, the two leading causes of death in the developed world.

The stiffer and harder the blood vessel walls, the higher the pulse pressure and the more the heart has to work to pump blood into the arteries. This increases the load on the heart, since it has to perform more work to maintain the stroke volume. Over time, this increased workload causes left ventricular hypertrophy and left ventricular remodeling, which can lead to heart failure. With increased arterial stiffness, also the microvasculature of brain and kidneys are exposed to wider pressure fluctuations, which may lead to increased risk of stroke and renal failure.

Arterial stiffening occurs as a consequence of biological aging but it can be accelerated by a number of risk factors including inflammation, mechanical stress, hypertension, and arteriosclerosis. At present there is no specific medication for arterial stiffness. Current treatment strategies employ antihypertension drugs, antihyperlipidemic agents, and exercise training.

Rebamipide, which is chemically 2-[(4-chlorobenzoyl) amino]-3-(2-oxo-1H-quinolin-4-yl)propanoic acid) is clinically used for the treatment of acute and/or chronic gastritis and gastric ulcers. The molecule has recently been described to suppress formation of atherosclerotic plaques by controlling lipid metabolism and inflammation and was suggested to be useful in the treatment of atherosclerosis and associated cardiovascular diseases in hyperlipidemic patients (Jhun J Y et al. Rebamipide ameliorates atherosclerosis by controlling lipid metabolism and inflammation. *PLoS ONE.* 2017; 12(2):e0171674). Jae Moon Choi A et al (Pharmacological Research, 2001, 43(5):489-495) reports on the effects of rebamipide on vasospasms induced by periarterial blood. The oral administration of rebamipide inhibited the increase in wall thickness and decrease in lumen area caused by periarterial blood. WO 2014/021637 discloses the effects of rebamipide in controlling lipid metabolism, inducing immune modulation ad reducing inflammation in atherosclerosis. Jung-Yoon Choe et al (Inflammation Research, 2010, 59(12):1019-1026) discloses the anti-inflammatory effects of rebamipide on the vasculature. Mozos Ioana et al (Frontiers in Immunology, 2017, 8:1058) reports on inflammatory markers for arterial stiffness in cardiovascular diseases.

SUMMARY OF THE INVENTION

It was surprisingly found that rebamipide has also other beneficial effects on the condition of arteries, unrelated to its antihyperlipidemic action. Following its long-term administration, a decrease in the stiffness of arteries has been observed by measuring the pulse wave velocity. The presumed mechanism of action is likely based on rebamipide's ability to restore the function of the endothelial cell-cell junctions in combination with its ability to suppress inflammation and stimulate secretion of protective glycoproteins, thereby protecting vascular endothelial barrier and decreasing vascular permeability.

The vascular endothelium is a barrier made of a thin layer of squamous cells lining the inner surface of the blood vessel wall of arteries, capillaries and veins. Barrier integrity and vascular permeability rely on the control of endothelial cell-cell junctions. It is protected by glycocalyx, which is a complex surface layer of sialic acid-containing glycoproteins, proteoglycans, and glycosaminoglycans that together create a scaffold on the apical surface of vascular endothelial cells. Glycocalyx shields the vascular wall from direct exposure to blood flow, contributes to the vascular permeability barrier and inhibits coagulation and leukocyte adhesion.

Glycocalyx may be easily disrupted by a number of mechanisms resulting in induction of a proinflammatory endothelial response that destabilizes the intercellular junctions causing disruption of the endothelial barrier and increased vascular permeability. This facilitates transendothelial migration of immune cells to the arterial intima and induction of vascular inflammation leading to structural changes in arterial wall through the breakdown of elastin by matrix metalloproteinases, accumulation of abnormal collagen, proliferation of smooth muscle cells, and changes in the composition of the extracellular matrix, thereby contributing to loss of elasticity and stiffening of the arterial wall.

Substantial research shows that rebamipide exhibits anti-inflammatory properties in a number of unrelated diseases. It was also reported to improve intercellular junctions (Yu Lai et al. Rebamipide Promotes the Regeneration of Aspirin-Induced Small-Intestine Mucosal Injury through Accumulation of β-Catenin. *PLoS One.* 2015; 10(7):e0132031). Furthermore, it increases mucin and mucin-like secretion in various tissues such as stomach (Iijima K et al. Rebamipide, a cytoprotective drug, increases gastric mucus secretion in human: Evaluations with endoscopic gastrin test. *Dig Dis Sci* 2009; 54:1500-1507), eyes (Urashima H et al. Rebamipide increases the amount of mucin-like substances on the conjunctiva and cornea in the N-acetylcysteine-treated in vivo model. *Cornea* 2004, 23:613-619) and intestine (Yasuda-Onozawa Y et al. Rebamipide upregulates mucin secretion of intestinal goblet cells via Akt phosphorylation. *Mol Med Rep.* 2017; 16(6):8216-8222). Since vascular glycocalyx shares a lot of similarities with mucin, I believe that rebamipide promotes its secretion by a similar mechanism. Restoration of glycocalyx, the main protective barrier of the vascular wall, contributes to a decrease in vascular permeability leading to suppression of inflammation, and thereby to inhibition or abrogation of the loss of elasticity of the vascular wall.

The present invention thus provides rebamipide or a pharmaceutical composition thereof for use in a method of prevention and/or treatment of arterial stiffness, especially in a person suffering from or being at risk of hypertension, heart failure, myocardial infarction, stroke, peripheral arterial disease, renal failure, and/or chronic kidney disease by decreasing arterial stiffness.

It is of a great advantage that rebamipide's activity is not limited to plaque removal in atherosclerotic patients as previously thought but that the molecule rather targets several different mechanisms leading to increase in arterial elasticity and improvement of arterial health. This broadens its possible use also to normolipidemic persons, i.e. those that do not suffer from either atherosclerosis or hyperlipidemia. Thus, in a preferred embodiment, rebamipide is for use in a person having normal blood lipid level.

"Rebamipide", as used herein, shall include all forms of this active ingredient, such as anhydrous form, hydrated or solvated form (e.g. hemihydrate form), crystalline forms; and pharmaceutically acceptable salts thereof.

"Prevention" or "preventive use" shall be understood herein as preventing or delaying the increase in arterial stiffness and associated diseases, such as hypertension, heart failure, myocardial infarction, stroke, peripheral arterial disease, renal failure, and chronic kidney disease.

"Treatment" shall be understood herein as a therapy that is able to abrogate, inhibit, slow or reverse the progression of arterial stiffness and/or associated diseases.

In the therapeutic indications as described in the present invention, rebamipide may be used in oral pharmaceutical forms such as tablets, capsules, dragees, granules, microgranules (sachets), orodispersible tablets or films, sublingual tablets, crushed tablets, oral solutions, oral suspensions, syrups, mouthwashes, rinses; or in rectal pharmaceutical forms such as suppositories and enemas; or in a form for parenteral administration such as injection or infusion. Preferably, the oral pharmaceutical form such as tablets, capsules, dragees and granules may be a form with enteric release, such as enteric sustained release or enteric controlled release.

A typical daily dose of rebamipide may range from 1 to 5000 mg for an average human (70 kg weight), more preferably from 50 to 2500 mg, even more preferably from 100 to 1000 mg, and most preferably from 600 to 900 mg. When immediate release formulation of rebamipide is administered, the daily dose is typically divided into several doses, which are administered separately. The daily dose may be divided into two to six separate doses taken twice daily or three times per day or four times per day or five times per day or six times per day. In a preferred embodiment the daily dose is divided into three separate doses administered three times per day, e.g. 200 mg dose administered three times per day. Alternatively, the whole daily dose can be taken at once, especially if it is in the form of a sustained release formulation, e.g. 600 mg dose administered once daily.

Hereinafter, the present invention will be described more specifically by the following working example. However, the following working example is provided only for illustration and thus the present invention is not limited to it.

EXAMPLE

Aging of cardiovascular system is associated with worsening of arterial cushion function resulting in higher pulse pressure (systolic-diastolic amplitude). Pulse wave velocity (PWV), i.e. velocity at which the blood pressure pulse propagates through the circulatory system, is the gold standard method for arterial stiffness quantification. It can be readily measured non-invasively in humans, is highly reproducible, and predicts future cardiovascular events and all-cause mortality independent of conventional cardiovascular risk factors.

Pulse wave travels along the arteries at a velocity rate, which varies according to wall elasticity: the less elastic the wall, the higher the velocity of PW propagation. PWV measures the time of travel of the pressure wave over a known distance and is calculated as the distance between the two positions of the pulse transducer divided by the time delay measured between pressure upstroke at each site.

To study the effect of rebamipide on arteries, a small study on patients suffering from arterial stiffness was performed. Patients having PWV higher than the normal value for their age category (see The Reference Values for Arterial Stiffness' Collaboration. Determinants of pulse wave velocity in healthy people and in the presence of cardiovascular risk factors: "establishing normal and reference values". *Eur Heart J* 2010; 31(19):2338-2350) without any evidence of either atherosclerosis or hyperlipidemia were randomly divided into two groups taking either rebamipide 200 mg (two 100 mg tablets) or placebo three times a day for a period of 12 months. Carotid to femoral PWV (cfPWV) was measured in both groups at 0, 3, 6, 9 and 12 months.

Assessment carried out after the end of the study revealed that arterial stiffness was gradually decreasing in the rebamipide taking group, while the placebo group didn't experience any change over the course of the study. The difference between both groups reached statistical significance. The results obtained from the study indicate that the administration of rebamipide supports regeneration of the arteries leading to a decrease in arterial stiffness, thereby preventing hypertension, cardiovascular diseases and associated disorders.

The invention claimed is:

1. A method for treatment of arterial stiffness comprising administering a pharmaceutically effective dose of rebamipide or a pharmaceutical composition thereof to a subject in need of such treatment.

2. The method of claim 1, wherein the subject suffers from or being at risk of hypertension, heart failure, myocardial infarction, stroke, peripheral arterial disease, renal failure, or chronic kidney disease.

3. The method of claim 1, wherein administration of rebamipide or a pharmaceutical composition thereof increases arterial elasticity in the subject.

4. The method of claim 1, wherein the subject has a normal blood lipid level.

5. The method of claim 1, wherein rebamipide is administered in a pharmaceutical form, selected from: (a) oral pharmaceutical forms, including tablets, capsules, dragees, granules, microgranules (sachets), orodispersible tablets or films, sublingual tablets, crushed tablets, oral solutions, oral suspensions, syrups, mouthwashes, rinses; or (b) rectal pharmaceutical forms, including suppositories and enemas; or (c) parenteral pharmaceutical forms, including injection or infusion.

6. The method of claim 5, wherein the oral pharmaceutical form is a form with enteric release, enteric sustained release or enteric controlled release.

7. The method of claim 5, wherein rebamipide is administered in a daily dose of 100 to 1000 mg.

8. The method of claim 2, wherein the subject has a normal blood lipid level.

9. The method of claim 3, wherein the subject has a normal blood lipid level.

10. The method of claim 2, wherein rebamipide is administered in pharmaceutical form, selected from: (a) oral pharmaceutical forms, including tablets, capsules, dragees, granules, microgranules (sachets), orodispersible tablets or films, sublingual tablets, crushed tablets, oral solutions, oral suspensions, syrups, mouthwashes, rinses; or (b) rectal pharmaceutical forms, including suppositories and enemas; or (c) parenteral pharmaceutical forms, including injection or infusion.

11. The method of claim 3, wherein rebamipide is administered in pharmaceutical form, selected from: (a) oral pharmaceutical forms, including tablets, capsules, dragees, granules, microgranules sachets, orodispersible tablets or films, sublingual tablets, crushed tablets, oral solutions, oral suspensions, syrups, mouthwashes, rinses; or (b) rectal pharmaceutical forms, including suppositories and enemas; or (c) parenteral pharmaceutical forms, including injection or infusion.

12. The method of claim 10, wherein the oral pharmaceutical form is a form with enteric release, enteric sustained release or enteric controlled release.

13. The method of claim 11, wherein the oral pharmaceutical form is a form with enteric release, enteric sustained release or enteric controlled release.

14. The method of claim 10, wherein rebamipide is administered in a daily dose of 100 to 1000 mg.

15. The method of claim 11, wherein rebamipide is administered in a daily dose of 100 to 1000 mg.

16. The method of claim 7, wherein rebamipide is administered in a daily dose of 600 to 900 mg.

17. The method of claim 14, wherein rebamipide is administered in a daily dose of 600 to 900 mg.

18. The method of claim 15, wherein rebamipide is administered in a daily dose of 600 to 900 mg.

* * * * *